(12) United States Patent
Shimizu et al.

(10) Patent No.: US 12,020,180 B2
(45) Date of Patent: Jun. 25, 2024

(54) INFORMATION PROCESSING DEVICE, INFORMATION PROCESSING METHOD, INFORMATION PROCESSING SYSTEM, DISPLAY DEVICE, AND RESERVATION SYSTEM

(71) Applicant: SONY CORPORATION, Tokyo (JP)

(72) Inventors: Itaru Shimizu, Tokyo (JP); Makoto Koike, Tokyo (JP)

(73) Assignee: SONY CORPORATION, Tokyo (JP)

( * ) Notice: Subject to any disclaimer, the term of this patent is extended or adjusted under 35 U.S.C. 154(b) by 200 days.

(21) Appl. No.: 16/629,343

(22) PCT Filed: Jul. 30, 2018

(86) PCT No.: PCT/JP2018/028439
§ 371 (c)(1),
(2) Date: Jan. 8, 2020

(87) PCT Pub. No.: WO2019/073661
PCT Pub. Date: Apr. 18, 2019

(65) Prior Publication Data
US 2021/0158228 A1 May 27, 2021

(30) Foreign Application Priority Data
Oct. 13, 2017 (JP) .................................. 2017-199063

(51) Int. Cl.
*G06Q 10/02* (2012.01)
*A61B 5/00* (2006.01)
(Continued)

(52) U.S. Cl.
CPC .............. *G06Q 10/02* (2013.01); *A61B 5/165* (2013.01); *G06Q 30/0201* (2013.01);
(Continued)

(58) Field of Classification Search
CPC .... G06Q 10/02; G06Q 30/0201; A61B 5/165; A61B 5/6803; A61B 2503/12; G06V 40/174
(Continued)

(56) References Cited

U.S. PATENT DOCUMENTS

2007/0066916 A1* 3/2007 Lemos .................... A61B 3/113
600/558
2013/0237157 A1* 9/2013 Phan .................... G06V 40/174
455/67.11
(Continued)

FOREIGN PATENT DOCUMENTS

CN 101999108 A 3/2011
CN 103914136 * 7/2014 ............... G06F 3/01
(Continued)

OTHER PUBLICATIONS

Lopez-Gil et al, Method for Improving EEG Based Emotion Recognition by Combining It with Synchronized Biometric and Eye Tracking Technologies in a Non-invasive and Low Cost Way, Frontiers in Computational Neuroscience (Aug. 19, 2016) (Year: 2016).*

(Continued)

*Primary Examiner* — Jeff Zimmerman
*Assistant Examiner* — Mark C Clare
(74) *Attorney, Agent, or Firm* — CHIP LAW GROUP

(57) ABSTRACT

Provided is an information processing device including a reaction information use unit configured to use reaction information indicating a reaction of a user to presented information in a case where use of the reaction information has been permitted.

16 Claims, 18 Drawing Sheets

(51) Int. Cl.
  *A61B 5/16* (2006.01)
  *G06Q 30/0201* (2023.01)
  *G06V 40/16* (2022.01)
(52) U.S. Cl.
  CPC ......... *A61B 5/6803* (2013.01); *A61B 2503/12* (2013.01); *G06V 40/174* (2022.01)
(58) Field of Classification Search
  USPC .......................................................... 705/5
  See application file for complete search history.

(56) References Cited

U.S. PATENT DOCUMENTS

| | | | | |
|---|---|---|---|---|
| 2014/0347272 | A1* | 11/2014 | Hernandez-Abrego | ..................... A63F 13/213 345/156 |
| 2015/0319119 | A1 | 11/2015 | Ryu | |
| 2016/0142767 | A1* | 5/2016 | Shigeta | .............. H04N 21/4788 725/12 |
| 2016/0189064 | A1* | 6/2016 | Mao | ................... G06Q 30/0631 705/5 |
| 2018/0114341 | A1* | 4/2018 | Tian | ....................... G06Q 10/02 |
| 2018/0367484 | A1* | 12/2018 | Rodriguez | .............. H04L 51/10 |
| 2019/0336724 | A1* | 11/2019 | Li | ......................... A61B 5/165 |

FOREIGN PATENT DOCUMENTS

| | | | | |
|---|---|---|---|---|
| CN | 103914136 | A | 7/2014 | |
| CN | 103914139 | A | 7/2014 | |
| CN | 104919485 | A | 9/2015 | |
| CN | 105247879 | A1 | 1/2016 | |
| EP | 3007456 | A1 | 4/2016 | |
| JP | 2008-027301 | A | 2/2008 | |
| JP | 2010225082 | * | 3/2009 | ............. G06F 17/30 |
| JP | 2010225082 | * | 10/2010 | ............. G06F 17/30 |
| JP | 2013020365 | * | 1/2013 | ............. A63F 13/42 |
| JP | 2013223038 | A | 10/2013 | |
| KR | 10-2013-0033520 | A | 4/2013 | |
| WO | 2014/192457 | A1 | 12/2014 | |

OTHER PUBLICATIONS

International Search Report and Written Opinion of PCT Application No. PCT/JP2018/028439, dated Oct. 30, 2018, 12 pages of ISRWO.

Office Action for IN Patent Application No. 202017000626, dated Mar. 31, 2022, 06 pages of Office Action.

* cited by examiner

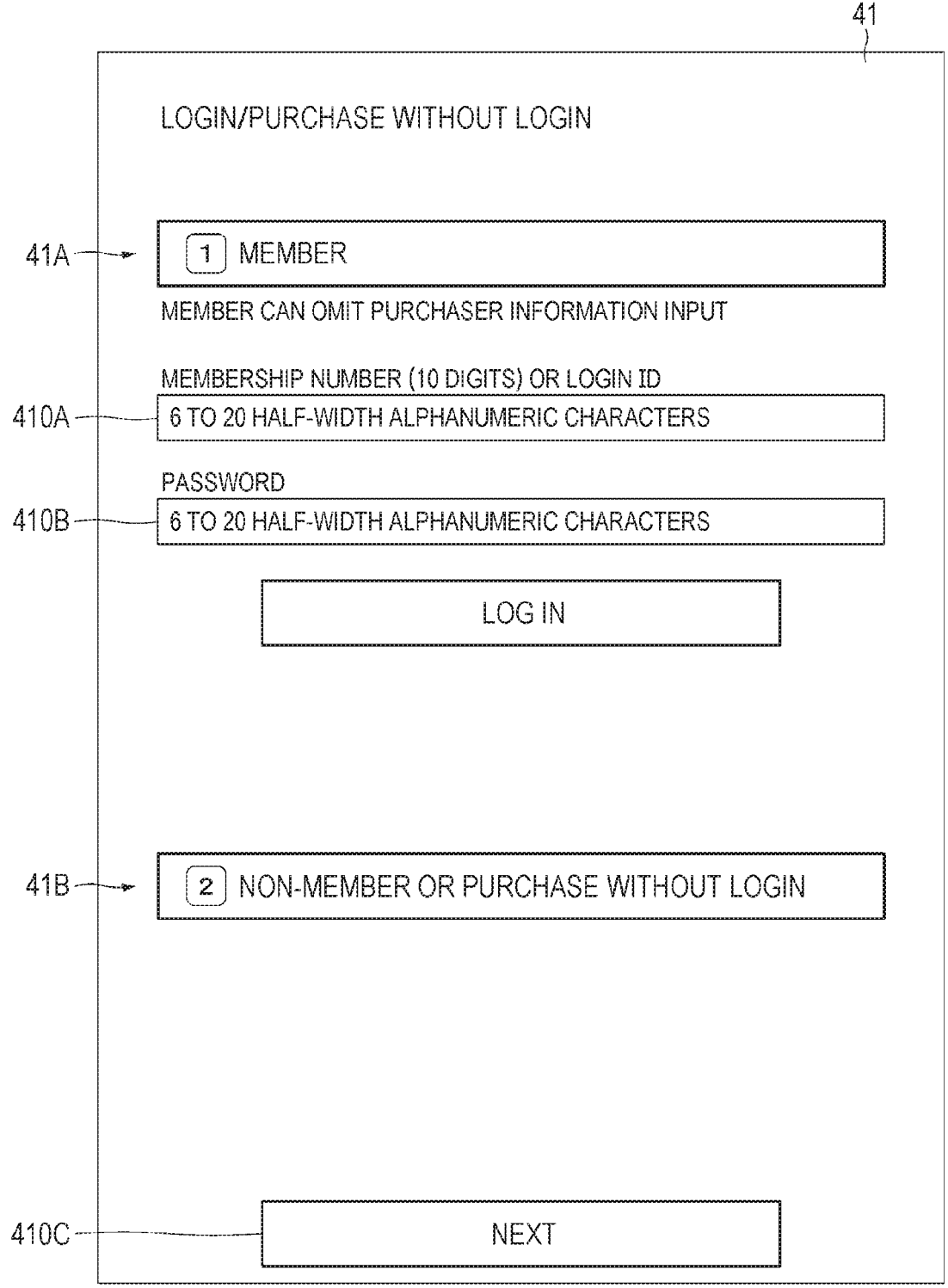

PLEASE ENTER INFORMATION NECESSARY FOR PURCHASE

CUSTOMER INFORMATION (*REQUIRED FIELD)

KANJI CHARACTER (FAMILY NAME) (*)
FAMILY NAME: EXAMPLE) NIPPON

KANJI CHARACTER (FIRST NAME) (*)
FAMILY NAME: EXAMPLE) TARO

GENDER (*)
○ MALE    ○ FEMALE

AGE (*)
[   ▼] YEARS OLD

TELEPHONE NUMBER (*REQUIRED FIELD)

HALF-WIDTH NUMERIC CHARACTERS
EXAMPLE) 0300000000

E-MAIL ADDRESS (*REQUIRED FIELD)

PC/SMARTPHONE
EXAMPLE) abc@defghijk.co.jp

RE-ENTER FOR CONFIRMATION
EXAMPLE) abc@defghijk.co.jp

PAYMENT METHOD (*REQUIRED FIELD)

○ CREDIT CARD    ○ BANK TRANSFER    ○ PAY AT CONVENIENCE STORE

IN THIS MOVIE, PERSONALITY ASSESSMENT BASED ON YOUR VIEWING/LISTENING STATE IS AVAILABLE (OPTIONAL)

45A → VIEWING/LISTENING TYPE ASSESSMENT | "EMOTION DURING VIEWING AND LISTENING" MAP | COMPATIBILITY CHECK

45B — • YOUR EMOTION WHILE VIEWING AND LISTENING OF MOVIE WILL BE ESTIMATED
RESULT OF EMOTION ESTIMATION MAY BE USED AS MARKETING INFORMATION (INDIVIDUAL WILL NOT BE IDENTIFIED)

45C — • OBTAINED PERSONAL INFORMATION WILL BE USED ONLY FOR PURPOSE OF THIS SERVICE AND WILL NOT BE PROVIDED TO THIRD PARTY
• YOUR EMOTION WILL NOT BE ESTIMATED WITHOUT CONSENT, AND OPTIONAL SERVICE ABOVE WILL NOT BE PROVIDED EITHER

45D — • 100Pt WILL BE GRANTED IF YOU RECEIVE SERVICE!

45E — ☐ I DO NOT AGREE TO TERMS OF THIS SERVICE AND I WILL NOT RECEIVE SERVICE

[ COMPLETE RESERVATION ]

FIG. 9

VOTE FOR CLIMAX!
WHICH OF FOLLOWING SCENES WILL BE MOST EXCITING IN THIS MOVIE?

| 1 | 2 | 3 |

✓ VOTE WILL BE AUTOMATICALLY CONDUCTED ACCORDING TO YOUR STATE DURING VIEWING AND LISTENING
✓ IF YOU PARTICIPATE IN "VOTE FOR CLIMAX", YOU WILL FIND OUT YOUR PERSONAL EXCITING SCENE

- YOUR EMOTION WHILE VIEWING AND LISTENING OF MOVIE WILL BE ESTIMATED

- OBTAINED PERSONAL INFORMATION WILL BE USED ONLY FOR PURPOSE OF THIS SERVICE AND WILL NOT BE PROVIDED TO THIRD PARTY

- YOUR EMOTION WILL NOT BE ESTIMATED WITHOUT CONSENT, AND OPTIONAL SERVICE ABOVE WILL NOT BE PROVIDED EITHER

☐ I DO NOT AGREE TO TERMS OF THIS SERVICE AND I WILL NOT RECEIVE SERVICE

[COMPLETE RESERVATION]

| CONTENT | SCENE | SEAT INFORMATION | EMOTION (SURPRISE) | EMOTION (SADNESS) | . . . |
|---|---|---|---|---|---|
| AA3 | 1 | 0035 | 4.0 | 10.0 | |
| AA3 | 2 | 0035 | 82.2 | 20.5 | |
| AA3 | 3 | 0035 | 30.5 | 78.4 | |

FIG. 20A

SCENE YOU WERE MOST SURPRISED IS...

| IM11 | ● AGREE
○ DISAGREE | 71

FIG. 20B

SYMPATHETIC SCENES

IM12

IM13

IM14

A'S ○○ SCENE

IM15

B'S ○○ SCENE

IM16

☆ COMPATIBILITY ○○% !! ☆  — 72

INFORMATION PROCESSING DEVICE, INFORMATION PROCESSING METHOD, INFORMATION PROCESSING SYSTEM, DISPLAY DEVICE, AND RESERVATION SYSTEM

CROSS REFERENCE TO RELATED APPLICATIONS

This application is a U.S. National Phase of International Patent Application No. PCT/JP2018/028439 filed on Jul. 30, 2018, which claims priority benefit of Japanese Patent Application No. JP 2017-199063 filed in the Japan Patent Office on Oct. 13, 2017. Each of the above-referenced applications is hereby incorporated herein by reference in its entirety.

TECHNICAL FIELD

The present disclosure relates to an information processing device, an information processing method, an information processing system, a display device, and a reservation system.

BACKGROUND ART

A device that captures images of attendees participating in an event, analyzes the result, and evaluates the event has been proposed (for example, see Patent Document 1 below).

CITATION LIST

Patent Document

Patent Document 1: Japanese Patent Application Laid-Open No. 2004-272529

SUMMARY OF THE INVENTION

Problems to be Solved by the Invention

In such a field, it is necessary to capture images of the attendees in the middle of the event, but it is not desirable to capture their images without permission from the viewpoint of protecting personal information.

Therefore, an object of the present disclosure is to provide an information processing device or the like that uses reaction information indicating a reaction of a user to presented information in a case where the user permits the use.

Solutions to Problems

The present disclosure is, for example,
an information processing device including:
a reaction information use unit configured to use reaction information indicating a reaction of a user to presented information in a case where use of the reaction information has been permitted.
The present disclosure is, for example,
an information processing method including:
by a reaction information use unit, using reaction information indicating a reaction of a user to presented information in a case where use of the reaction information has been permitted.
The present disclosure is, for example,
an information processing system including:
a reaction information acquisition unit configured to acquire reaction information indicating a reaction of a user to presented information; and
a reaction information use unit configured to use the reaction information in a case where use of the reaction information has been permitted.
The present disclosure is, for example,
a display device including:
a display control unit configured to perform control of displaying, on a display unit, seat information at the time of appreciating predetermined presented information, an input screen as to whether or not to permit use of reaction information indicating a reaction of a user at the time of appreciating the presented information, and information for prompting the permission, in a series of reservation processing for reserving a seat indicated by the seat information. Furthermore, the present disclosure is, for example,
a reservation system including:
the display device described above; and an information processing device connected to the display device, in which
the information processing device includes a reservation information management unit that manages permission information indicating presence or absence of the permission output from the display device and the reserved seat information in association with each other.

Effects of the Invention

According to at least an embodiment of the present disclosure, an information processing device and the like that use reaction information of a user in a case where the user permits the use can be provided. Note that effects described here are not necessarily limited, and any of effects described in the present disclosure may be exhibited. Furthermore, content of the present disclosure is not construed in a limited manner by the exemplified effects.

BRIEF DESCRIPTION OF DRAWINGS

FIG. 4 is a diagram illustrating an example of a screen in the reservation processing according to the embodiment.

FIG. 5 is a diagram illustrating an example of the screen in the reservation processing according to the embodiment.

FIG. 7 is a diagram illustrating an example of the screen in the reservation processing according to the embodiment.

FIG. 8 is a diagram illustrating an example of the screen in the reservation processing according to the embodiment.

FIG. 9 is a diagram illustrating an example of the screen in the reservation processing according to the embodiment.

FIGS. 20A and 20B are diagrams for describing another example of the service information.

MODE FOR CARRYING OUT THE INVENTION

Hereinafter, an embodiment and the like of the present disclosure will be described with reference to the drawings. Note that the description will be given in the following order.

<1. Embodiment>
1. Information processing system
1-1. Description of terms
1-2. System configuration example
1-3. Configuration example of reservation terminal
1-4. Server configuration example
1-5. Configuration example of reaction information acquisition device
1-6. Overview of processing in information processing system
2. Reservation processing
2-1. Flow of reservation processing
2-2. Screen example in reservation processing
3. Acquisition of emotion information at time of viewing and listening of movie
3-1. Arrangement example of sensor unit
3-2. Operation of emotion estimation unit
4. Generation of service information
4-1. Flow of processing after viewing and listening of movie
4-2. Operation example of service information generation unit
4-3. Specific example of service information
5. Processing in a case where there is no permission to use reaction information
<2. Modification>

Note that the embodiment and the like to be described below include preferred specific examples of the present disclosure, and content of the present disclosure is not limited to the embodiment and the like.

1. Embodiment

[1. Information processing system]
(1-1. Description of terms)
First, main terms used in the present embodiment will be described.

"Presented information" refers to information presented to a user, and viewed and listened to, appreciated, watched, or the like by the user. In the present embodiment, the presented information will be described using content, more specifically, a movie as an example.

"Sensor information" refers to information (data) obtained by a sensor device such as a camera module or a biological sensor.

"Reaction information" refers to information indicating a reaction of a user to the presented information, and specifically refers to information obtained by analyzing the sensor information. In the present embodiment, information corresponding to an emotion is used as the reaction information. Therefore, the "reaction information" may be referred to as "emotion information". Note that the "reaction information" includes not only an emotion but also presence/absence of a reaction and a change in a state of the user, and is a wider concept than the "emotion information".

"Permission information" refers to information indicating presence or absence of permission regarding use of the "reaction information".

"Service information" refers to information presented to the user who has permitted the use of the "reaction information".

Figure 1:
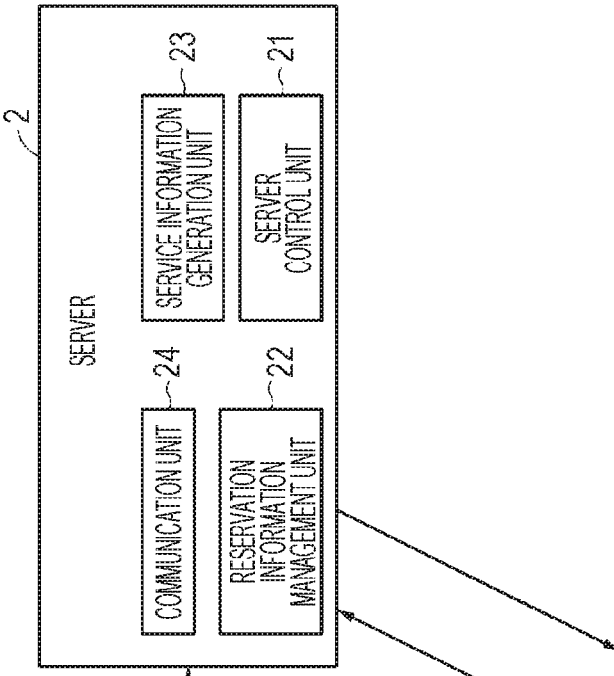
FIG. 1 is a block diagram illustrating a configuration example of an information processing system according to an embodiment.

(1-2. System Configuration Example)
FIG. 1 illustrates a configuration example of an information processing system (information processing system 100) according to the present embodiment. The information processing system 100 includes, for example, a reservation terminal 1, a server 2 that is an example of an information processing device, and a reaction information acquisition device 3. For example, the reservation terminal 1 and the server 2 constitute a reservation system.

(1-3. Configuration Example of Reservation Terminal)
Next, a schematic configuration example of each device will be described. First, a configuration example of the reservation terminal 1 will be described. The reservation terminal 1 may be a terminal installed in a public place or a store or may be a personal computer, a smartphone, a tablet computer, or the like that a user U has. In the present embodiment, the reservation terminal 1 will be described using a smartphone owned by the user U as an example.

The reservation terminal 1 that is an example of a display device includes, for example, a reservation terminal control unit 11 that is an example of a display control unit, a display unit 12, and a communication unit 13. The reservation terminal control unit 11 is configured by a central processing unit (CPU), and controls each unit of the reservation terminal 1. The display unit 12 is configured by a liquid crystal display (LCD), an organic electro luminescence (EL) panel, and the like. The display unit 12 according to the present embodiment is configured as a touch screen that can accept an operation input to the display unit 12. The communication unit 13 communicates with the server 2 or the like via the Internet or the like. Note that the reservation terminal 1 may have a known configuration in addition to the above-described configuration.

(1-4. Server configuration example)
The server 2 includes, for example, a server control unit 21, a reservation information management unit 22, a service information generation unit 23 that is an example of a reaction information use unit, and a communication unit 24. The server control unit 21 is configured by a CPU, for example, and controls each unit of the server 2.

The reservation information management unit 22 is a storage unit or the like that manages reservation information based on information input to the reservation terminal 1. For example, the reservation information management unit 22 manages an ID of the user U, attribute information of the user U, seat information indicating a seat reserved by the user U, and permission information in association with one another. The attribute information of the user U is information indicating attributes of the user U, and is, for example, gender, nationality, residential area, race, age, and the like of the user U. Note that the attribute information of the user U may be input at the time of seat reservation or may be registered in advance before reservation.

The reaction information according to the present embodiment is information indicating a reaction of the user U to the movie, and is more specifically an emotion of the user U while watching the movie. The emotion is a concept including mental states such as sleepiness, empathy, relaxation, excitement, and concentration, as well as delight, anger, sorrow and pleasure emotions. The emotion is not limited to one directly detected as the sensor information but may be one estimated on the basis of the sensor information. For example, Russell's emotional ring model is known as a model in which a plurality of emotions is mapped. In the Russell's emotional ring model, various emotions are estimated on the basis of two indicators of a pleasant state and an arousal state. The emotions may be classified according to such an emotion estimation model.

The service information generation unit 23 generates service information provided to the user U who has permitted the use of the reaction information. The service information is generated on the basis of the reaction information of the user U. Details of the service information will be described below. The user U who has permitted the use of the reaction information can obtain the service information during or after viewing and listening of a movie, for example. The communication unit 24 communicates with the reservation terminal 1, the reaction information acquisition device 3, and the like via the Internet or the like.

(1-5. Configuration Example of Reaction Information Acquisition Device)

The reaction information acquisition device 3 includes a control unit 31, a sensor unit 32, an emotion estimation unit 33, and a communication unit 34. For example, the sensor unit 32 and the emotion estimation unit 33 constitute a reaction information estimation unit. The control unit 31 is configured by a CPU, for example, and controls each unit of the reaction information acquisition device 3. The sensor unit 32 is a sensor that measures the state (reaction) of the user U at the time of viewing and listening of a movie, for example. The sensor unit 32 according to the present embodiment includes, for example, a camera module 32A and a biosensor 32B. However, a configuration based only on the camera module 32A or a configuration based only on the biosensor 32B may be adopted. The camera module 32A is a device that captures images of the user U who is watching a movie, and has a configuration including: a lens 321; an image sensor 322 including a charge coupled device (CCD), a complementary metal oxide semiconductor (CMOS), or the like; an image processing unit 323; and a camera control unit 324 that controls the entire camera module 32A. The biosensor 32B is a sensor that measures bio-information of the user U. Examples of the bio-information of the user U include user U's body temperature, heart rate, pulse, blood pressure, sweating, brain waves, body movement, and the like.

The emotion estimation unit 33 estimates (analyzes) the emotion of the user U on the basis of the sensor information measured by the sensor unit 32. The communication unit 34 communicates with the server 2 or the like via the Internet or the like.

(1-6. Overview of Processing in Information Processing System)

Figure 2:
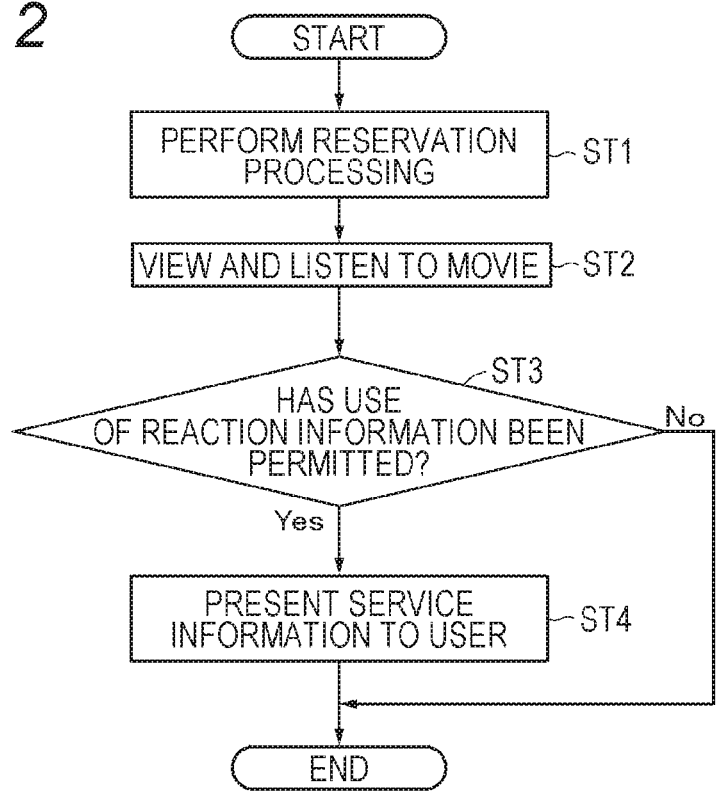
FIG. 2 is a flowchart illustrating a flow of processing in the information processing system according to the embodiment.

Processing performed in the information processing system 100 will be schematically described with reference to the flowchart illustrated in FIG. 2. In step ST1, reservation processing in which the user makes a reservation for a movie using the reservation terminal 1 is performed. The user U designates a movie to be viewed and listened to and designates a seat as a viewing position. The user U further inputs the permission information indicating whether or not to permit use of the reaction information. The use of the reaction information means that the reaction information is used as marketing information for developing new customers, grasping the tendency of movie preferences, selling movies related products, and the like. The reservation information input via the reservation terminal 1 is transmitted to the server 2 by communication. The server 2 manages the reservation information transmitted from the reservation terminal 1. Then, the processing proceeds to step ST2.

In step ST2, the user U views and listens to the movie that the user U has reserved in a movie theater. The reaction of the user U at the time of viewing and listening of the movie is estimated by the reaction information acquisition device 3 installed in the movie theater. Then, the estimation result is transmitted from the reaction information acquisition device 3 to the server 2. Then, the processing proceeds to step ST3.

In step ST3, whether or not the user U has permitted the use of the reaction information is determined. In a case where the user U has not permitted the use of the reaction information in this determination processing, the processing ends. On the other hand, in a case where the user U has permitted the use of the reaction information, the processing proceeds to step ST4.

In step ST4, the server 2 refers to the seat information and the permission information, and generates the service information for the user U who has permitted the use of the reaction information. This service information is presented to the user U. Then, the processing ends.

[2. Reservation Processing]

(2-1. Flow of Reservation Processing)

Figure 3:
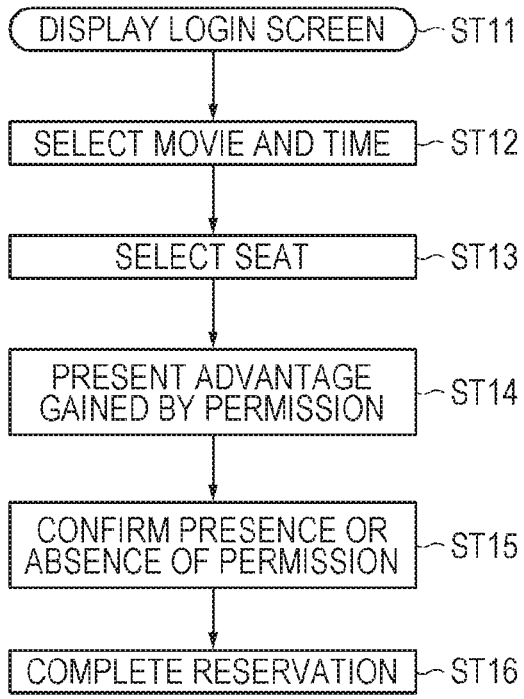
FIG. 3 is a flowchart illustrating a flow of reservation processing according to the embodiment.

Next, specific content of each processing will be described. FIG. 3 is a flowchart illustrating a flow of reservation processing according to the present embodiment. In step ST11, a login screen is displayed on the display unit 12 of the reservation terminal 1. Then, the processing proceeds to step ST12. In step ST12, the movie and a screen time are designated Then, the processing proceeds to step ST13. In step ST13, a seat is selected. Then, the processing proceeds to step ST14. In step ST14, an expected influence on the user gained by permitting the use of the reaction information is displayed, and, in particular, an advantage (merit) obtained by the user is displayed. Then, the processing proceeds to step ST15. In step ST15, the presence or absence of permission is confirmed. Then, the processing proceeds to step ST16. In step ST16, the movie reservation is completed.

(2-2. Screen Example in Reservation Processing)

A specific example of each processing will be described. Here, a screen example in the reservation processing will be described. The screen example described below is displayed on the display unit 12 in accordance with the control of the reservation terminal control unit 11.

The user U is connected to a reservation page using a dedicated site or a specific application using the reservation terminal 1. FIG. 4 illustrates an example of a login screen 41 displayed on the display unit 12 of the reservation terminal 1 in step ST11. An input item 41A for members and an input item 41B for non-members are displayed on the login screen 41, for example. The input item 41A for members includes a display 410A for inputting a membership number and a display 410B for inputting a password. Note that, in the present embodiment, attribute information of the member is registered in advance in the case of a member, and input of attribute information required for a non-member can be omitted in the case of logging in as a member. After making a necessary input on the login screen 41, the user U selects a display 410C of "Next".

In a case where the non-member, that is, a purchase has been selected without login on the login screen 41, a purchaser information input screen 42 illustrated in FIG. 5 is displayed, for example. Fields for inputting information necessary for purchasing the movie, such as a name, a telephone number, contact information such as an e-mail address, a payment method, and the like are displayed on the purchaser information input screen 42 illustrated in FIG. 5. Moreover, fields for inputting the attribute information (for example, gender and age) of the user U are displayed on the purchaser information input screen 42.

Figure 6:
FIG. 6 is a diagram illustrating an example of the screen in the reservation processing according to the embodiment.

FIG. 6 illustrates an example of a movie selection screen 43 for designating a movie in step ST12. Information including, for example, a movie theater name (for example, Tokyo Movie Theater AB), a movie name (movie AAA), a screen date (May 1st (Monday)), a plurality of screen start times, a running time, availability of reservation, and the like is displayed on a movie selection screen 43. The user U selects an available movie using the movie selection screen 43.

Figure 7:
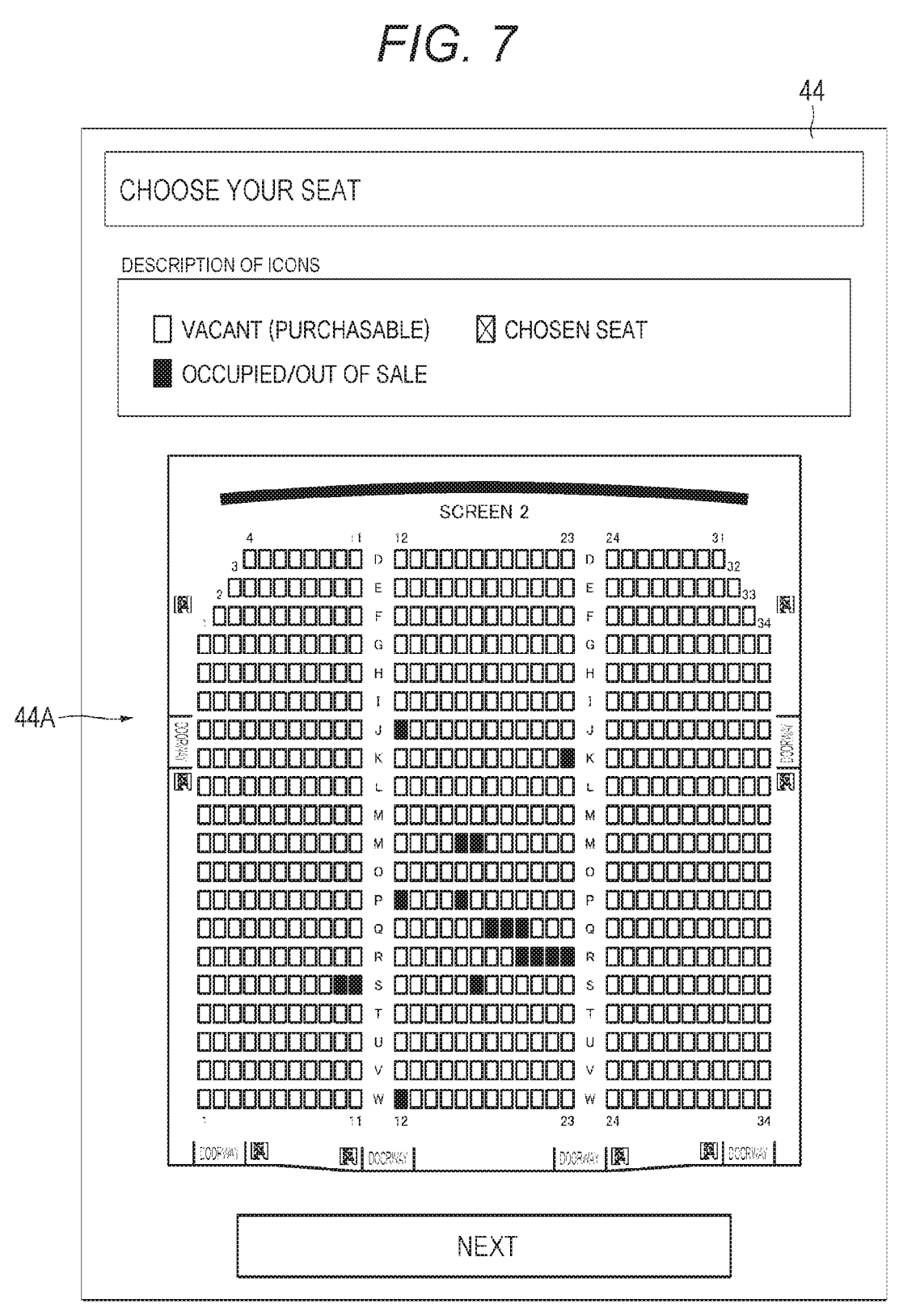

FIG. 7 illustrates an example of a seat selection screen 44 displayed on the display unit 12 in the processing of selecting a seat in step ST13. A seat display 44A including seat arrangement, available seat positions, selected seats, and the like is displayed on the seat selection screen 44, for example. The user U selects and reserves a desired seat with reference to the seat display 44A. Note that a plurality of seats may be reserved corresponding to the logged-in user U, more specifically to one account corresponding to the user U. In the case where a plurality of seats is reserved, it may be estimated that a predetermined relationship exists among a plurality of users U who uses the seats. For example, in a case where two seats are reserved for one account, the users U who use the respective seats may be estimated to be lovers, a couple, or friends, and in a case where three or more seats are reserved for one account, the users U who use the respective seats may be estimated to be family members or friends. Note that, in the case of reserving two or more seats for one account, input of not only the user U having the account but also attribute information of other users U who are related to the reservation can be requested.

FIG. 8 illustrates an example (screen 45) of a screen displayed on the display unit 12 in the processing in step ST13. A display 45A indicating that a personality assessment, specifically, a viewing/listening type assessment, a map of emotion during viewing, a compatibility check, and the like can be provided after viewing and listening of the movie is displayed on the screen 45 as the service information. The user U selects desired service information from the display 45A. Note that the compatibility check may be made selectable in a case where a plurality of seats is reserved for one account.

To generate the service information, emotion information is acquired as emotion estimation of the user U is performed at the time of viewing and listening of the movie, and a display 45B indicating that the emotion information can be used for the marketing information is displayed on the screen 45. More specifically, the screen 45 may display an indication that an image of user U is to be captured or the bio-information is to be measured. Furthermore, a display 45C including a display regarding disclaimers that information will not be used for unintended use, the information will be used without being associated with the user U by statistical processing, and the like, and a display that the emotion estimation will not be performed without consent of the user U and the service information will not be presented is displayed on the screen 45.

There may be a user U who feels psychological resistance to capturing images or acquiring the bio-information at the time of viewing and listening of a movie, among the users U. Therefore, it is favorable to display (display regarding incentives) prompting the user U to permit use of the emotion information in addition to presentation of the service information. A display 45D informing that 100 points will be added in addition to presentation of the service information in the case where the user permits use of the emotion information is displayed on the screen 45 according to the present embodiment.

Of course, the user U is not forced to receive the emotion estimation at the time of viewing and listening of a movie. In a case where the user U does not wish to be presented the service information, the user U is only required to check a check box for disagreement included in a display 45E. Furthermore, in a case where the user receives a service regarding the presentation of the service information, a display informing that personal information specifically specifying the individual user U will not be acquired may be displayed.

Furthermore, the screen 45 regarding the service information may be a trial play screen for a quiz or the like regarding the movie as illustrated in FIG. 9. In a screen example 46 illustrated in FIG. 9, a quiz for predicting a most exciting scene in the movie is displayed. An answer to the quiz is determined on the basis of the emotion information of a plurality of users U during viewing and listening of the movie, and a result is fed back to the user U who has permitted the use of the emotion information after viewing and listening of the movie. The screen examples illustrated in FIGS. 8 and 9 may be displayed in time series or simultaneously. Furthermore, not the quiz regarding the movie but content for prompting the user to input previous expectation for the movie may be displayed. By providing the trial play screen before viewing and listening of the movie, an effect of prompting the user U to permit the use of the emotion information can be expected, and comparison between reactions based on the emotion estimation during viewing and listening of the movie with expected values before viewing and listening of the movie can be presented in presenting the reactions after viewing and listening of the movie, thereby further attracting the user U's interest. Moreover, comparison information between the expectations and predictions before viewing and listening and the results of actual emotion estimation is also useful information from the viewpoint of marketing.

The reservation information input using the reservation terminal 1 is transmitted from the communication unit 13. Then, the reservation information is received by the communication unit 24 of the server 2 and managed by the reservation information management unit 22 of the server 2.

[3. Acquisition of Emotion Information at Time of Viewing and Listening of Movie]

(3-1. Arrangement Example of Sensor Unit)

Figure 10A:
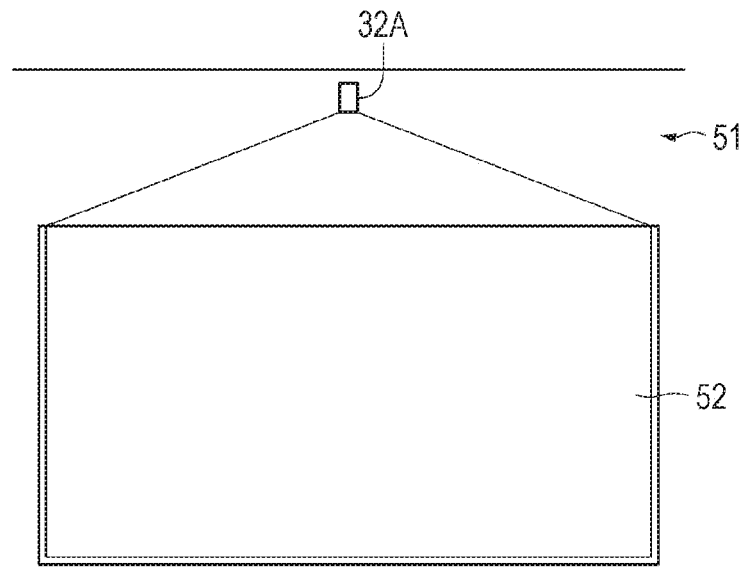
FIGS. 10A and 10B are diagrams for describing an arrangement example of camera modules according to the embodiment.
Figure 10B:
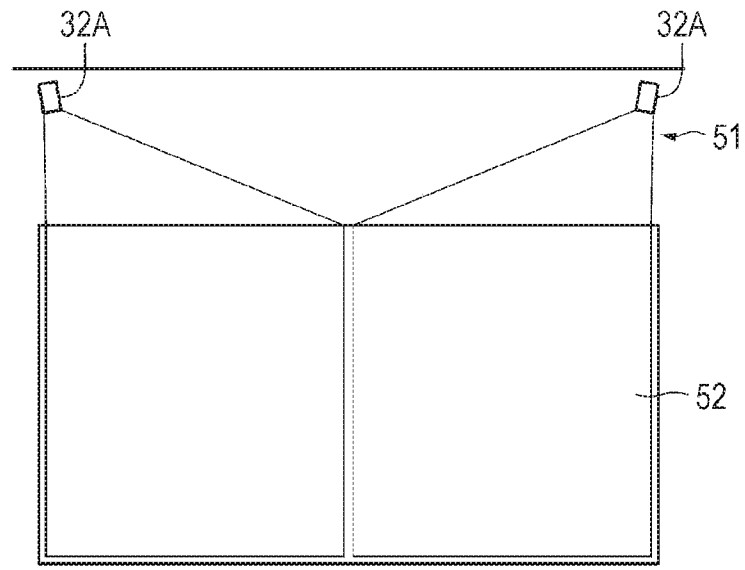

The user U actually views and listens to the movie after the reservation processing. FIGS. 10A and 10B illustrate arrangement examples of the camera module 32A of the sensor unit 32. The camera module 32A is arranged in a predetermined theater 51 in the movie theater. For example, as illustrated in FIG. 10A, the camera module 32A is arranged at a front (a screen side) of the theater 51 toward seats 52. As illustrated in FIG. 10B, the seats 52 may be divided into a plurality of areas (for example, two areas), and the camera module 32A may be arranged for each area. As a result, the resolution for each user to be captured by one camera module can be secured. Furthermore, a plurality of camera modules 32A may capture images of a common area from different angles. Thereby, even in a case where the user moves, a facial expression or the like can be accurately recognized. A plurality of camera modules 32A arranged close to one other in an array manner may be used for one area. Images of the user U existing in a capture range are captured on the basis of an image obtained by the camera module 32A, and other processing such as recognition of the face of the user U is performed.

Figure 11:
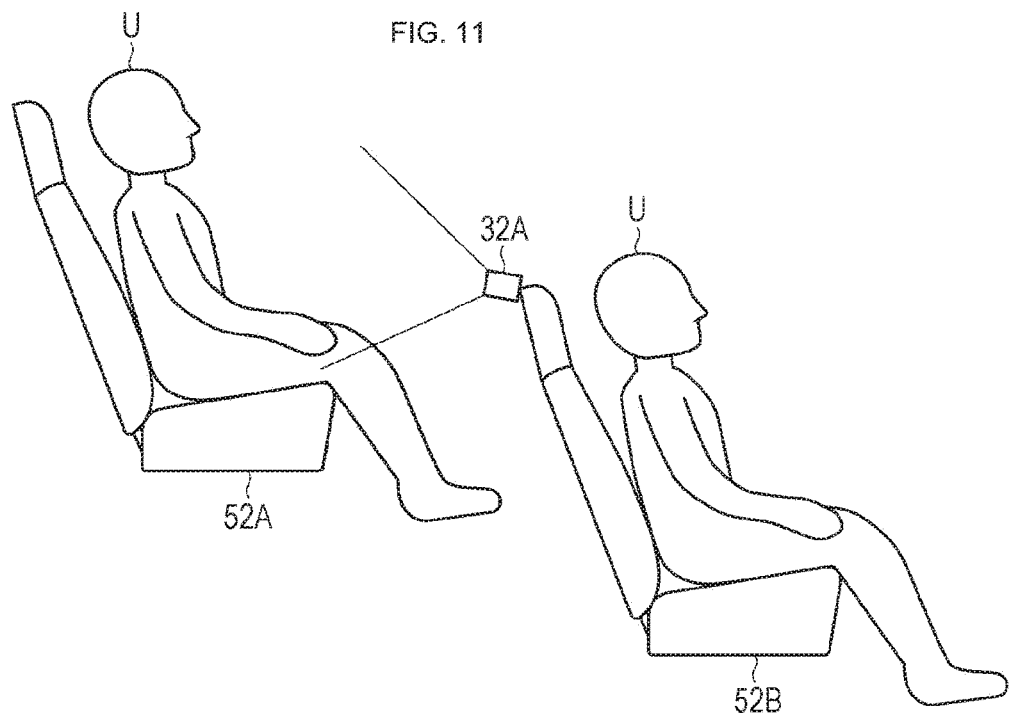
FIG. 11 is a diagram for describing another arrangement example of the camera modules according to the embodiment.

The camera module 32A may be provided for each seat as illustrated in FIG. 11 FIG. 11 illustrates a seat 52A and a seat 52B in front of the seat 52A of all of seats. Generally, seats in movie theaters are provided such that the seat 52A on the back side is located higher than the front seat. The camera module 32A may be provided near a backrest of the seat 52B and capture images of the user U on the seat 52A. Note that a plurality of camera modules 32A may be provided for each seat. By providing the camera module 32A for each seat, the user's facial expression and the like can be more accurately detected.

Figure 12A:
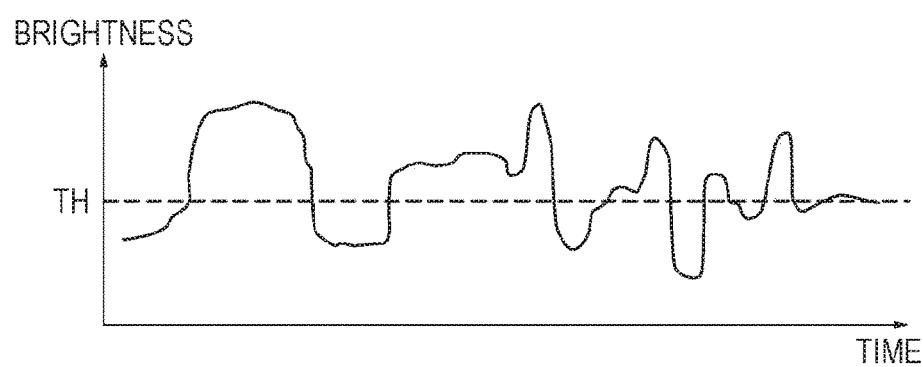
FIGS. 12A and 12B are diagrams for describing a setting example of the camera modules according to the embodiment.
Figure 12B:
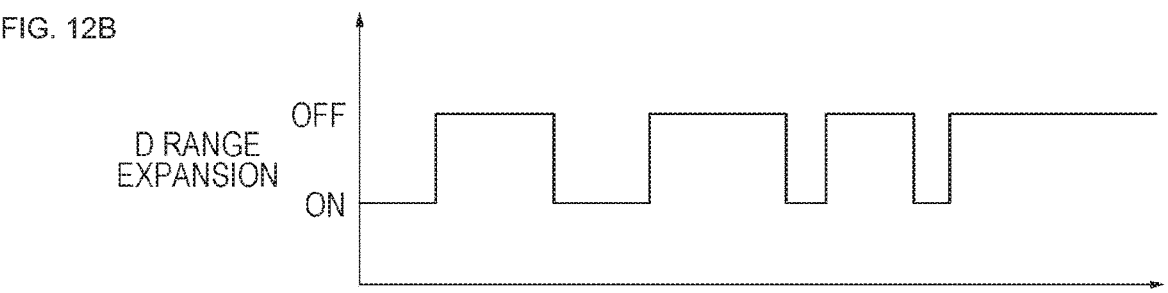

A setting value of the camera module 32A may be fixed or may be made variable in synchronization with the progress of the movie. As an example of the case of making the setting value of the camera module 32A variable, the setting value can be changed according to brightness of the movie, as illustrated in FIGS. 12A and 12B. An example of the setting value includes a dynamic range. FIG. 12A is a diagram schematically illustrating the brightness that changes with the progress of the movie. The horizontal axis represents time and the vertical axis represents the brightness. FIG. 12B is a diagram temporally corresponding to FIG. 12A, illustrating the dynamic range that is changed with a change in the brightness. For example, in a case where the lightness exceeds a threshold value TH, processing of expanding the dynamic range is performed according to the control of the camera control unit 324. Thereby, even if the brightness changes depending on the scene of the movie, the facial expression of the user U can be accurately detected. Note that the camera module 32A may detect the change in the brightness in real time using a sensor or the like, may detect the change in the brightness on the basis of the captured image, or may read the change in stored brightness that has been measured in advance at an opportunity of, for example, test playback of the movie.

The setting value is not limited to the dynamic range, and may be sensitivity of the image sensor 322, a frame rate of the image sensor 322, a shutter speed, a resolution, or a combination thereof. As a change other than the brightness, a user's movement can be considered, for example, and in a case where the user's movement is detected, the shutter speed can be changed as a setting value. Furthermore, it is not necessary for the camera module 32A to capture an image on a constant basis during movie playback, and may capture an image only during a set period. Furthermore, an image may be captured in a single color instead of color, or infrared rays may be detected.

Figure 13:
FIG. 13 is a diagram for describing an arrangement example of a biosensor according to the embodiment.

The biosensor 32B detects the user U's body temperature, heart rate, pulse, blood pressure, sweating, brain waves, body movement, and the like. As illustrated in FIG. 13, the biosensor 32B is built in, for example, 3D glasses 53A lent at the movie theater. The sensor mounted in the biosensor 32B favorably detects the temperature, pulse, sweating, brain waves, and body movement, for example. The biosensor 32B may be built in a seat 53B, and may be, for example, a pressure sensor, a temperature sensor, a pulse wave sensor, a heart rate sensor, a brain wave sensor, or a combination thereof. Furthermore, the biosensor 32B may be a device that is lent to the user U who has permitted the use of the reaction information. The biosensor 32B may be provided in a front seat (for example, a thermography or a sensor using reflection of radio waves) like the camera module 32A illustrated in FIG. 11. Furthermore, in recent years, some devices such as wristbands and smartphones, and clothes such as shirts owned by the user U have a function to measure the bio-information of the user U. The reaction information acquisition device 3 may acquire the bio-information of the user U from such a device by short-range wireless communication or the like. Logs of other emotion estimation services that are regularly used by the user may be used. In this case, an instruction prompting the user U to connect the device owned by the user U with the reaction information acquisition device 3 may be presented, or the short-range wireless communication may be established according to the proximity between the device owned by the user U and the seat constituting the reaction information acquisition device 3 and the bio-information of the user U may be automatically acquired via the short-range wireless communication.

(3-2. Operation of Emotion Estimation Unit)

The sensor information obtained by the camera module 32A and the biosensor 32B is supplied to the emotion estimation unit 33. The emotion estimation unit 33 estimates an emotion of the user on the basis of the sensor information. A known method can be applied to the method of estimating the emotion on the basis of the sensor information. For example, the emotion estimation unit 33 estimates the emotion of the user U from characteristic points of the captured user's face and postures of the user included in the sensor information. More specifically, the emotion estimation unit 33 performs face recognition based on the sensor information and facial expression analysis of the recognized face, and obtains element values necessary for the emotion estimation from the results. For example, a smile degree indicating the degree of smile may be obtained, and an absolute value of the smile degree may be estimated as the degree of a certain emotion (for example, "joy"), or in a case where the smile degree exceeds a predetermined threshold value, the user may be determined to be in a certain "joy" state. Alternatively, a final emotion may be estimated by specifying a ratio of a plurality of elementary emotions or a dominant elementary emotion among the plurality of elementary emotions. Alternatively, an arbitrary emotion may be estimated directly from the facial expression recognized using machine learning or the like, regardless of the elemental emotion. Here, when estimating the emotion, the emotion can be more accurately estimated by referring to the bio-information included in the sensor information. Alternatively, the emotion estimation can be performed on the basis of only the information from the biosensor 32B without capturing images using the camera module 32A.

Figure 14A:
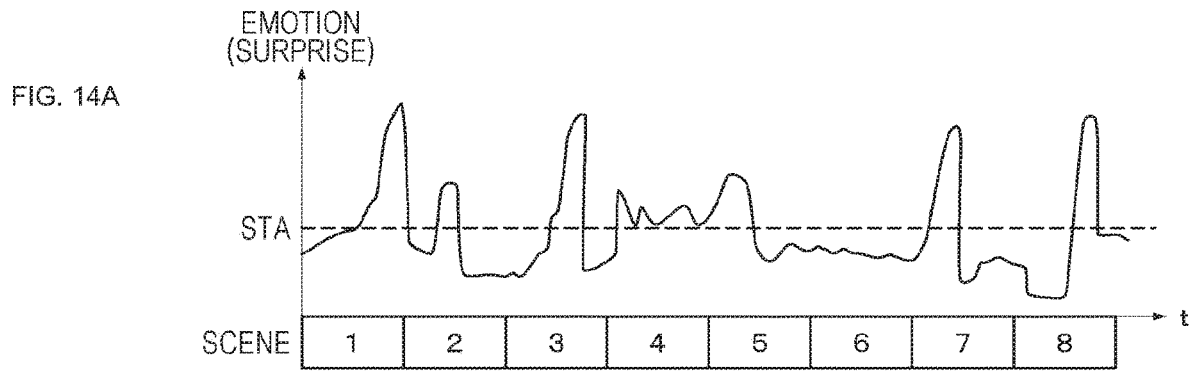
FIGS. 14A, 14B, and 14C are diagrams for describing a plurality of examples of emotion estimation methods by an emotion estimation unit according to the embodiment.
Figure 14B:
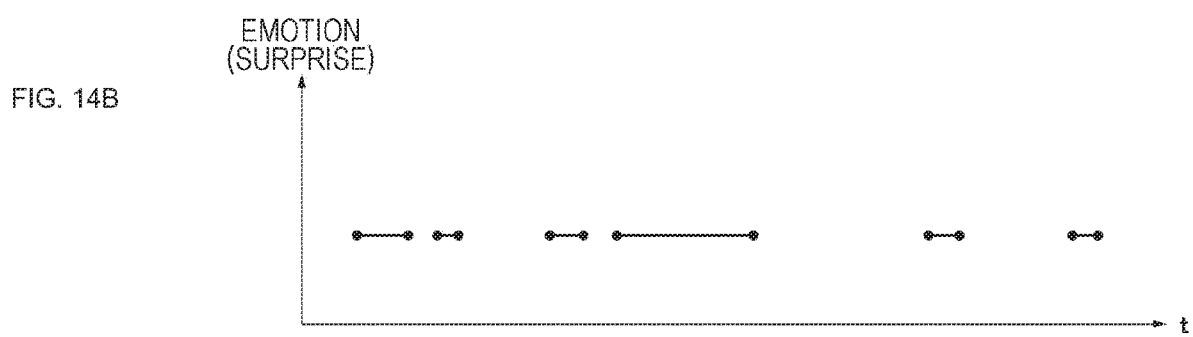
Figure 14C:
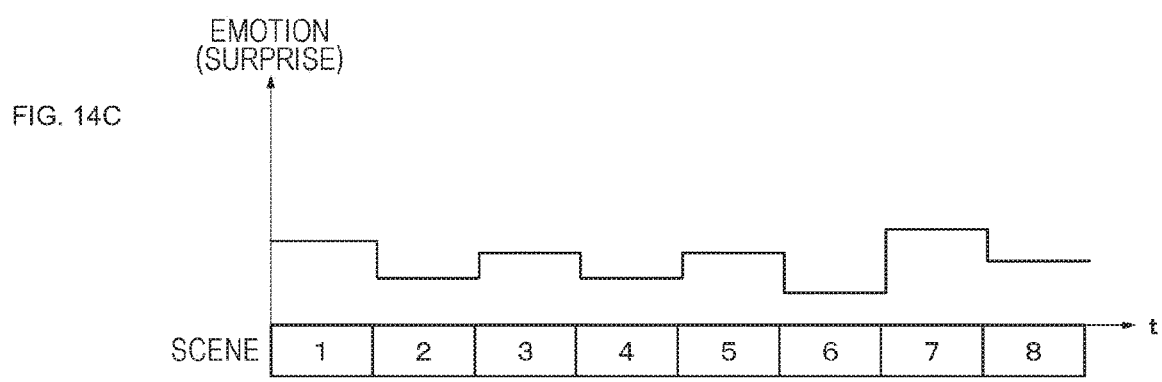

FIGS. 14A, 14B, and 14C illustrate examples of emotion estimation results by the emotion estimation unit 33. For example, as illustrated in FIG. 14A, a change in an estimated value corresponding to a certain emotion (for example, surprise) is set as a result of the emotion estimation. Note that FIGS. 14A, 14B, and 14C will be described using surprise as an example. However, other emotional changes are also estimated in a similar manner. The result of the emotion estimation can be estimated in real time for each predetermined frame rate. For example, strength of a level of the emotion is derived as a curve as illustrated in FIG. 14A. The method of presenting the result of the emotion estimation is not limited to the change in the level of the emotion. For example, as illustrated in FIG. 14B, a period in which the estimated value corresponding to the surprise emotion exceeds a reference value STA (see FIG. 14A) may be presented as being in a surprise state. By presenting the result in this way, the result of the emotion estimation can be referred as a binary value as to whether or not the user U is in the surprise state. Furthermore, as illustrated in FIG. 14C, an average value of the estimated values corresponding to the surprise emotion may be set for each scene as a result of the emotion estimation. By presenting the result in this way, the emotion of the user U can be evaluated for each scene. At this time, the reference value STA illustrated in FIG. 14A may be made different for each scene.

The estimated value corresponding to a certain emotion may be a relative value to an average of all of users for a certain scene of the movie. The average value to be compared is, for example, a value obtained corresponding to a specific scene (reference scene) that is generally easy to recall a specific emotion in the movie. The reference scene may be provided for each emotion to be estimated. For example, for "joy", a predetermined scene determined that many users U are likely to have a feeling of joy is used as the reference scene, and for "sadness", a predetermined scene determined that many users U are likely to have a feeling of sadness can be used as the reference scene. Furthermore, the estimated value corresponding to a certain emotion may be an average value within a unit time or a variation value within a unit time instead of each scene.

Note that the emotion estimation based on the sensor information may not be able to be appropriately performed depending on the posture, appearance, or the like of the user U. For example, in a case where the user U's face is captured by the camera module 32A and the user's face is hidden by a hat, sunglasses, or the like, the emotion estimation by the emotion estimation unit 33 cannot be appropriately performed. In such a case, metadata indicating that the emotion estimation could not be performed is stored in association with a corresponding scene. Alternatively, metadata indicating the accuracy of the emotion estimation may be stored.

Figures 15, 16:
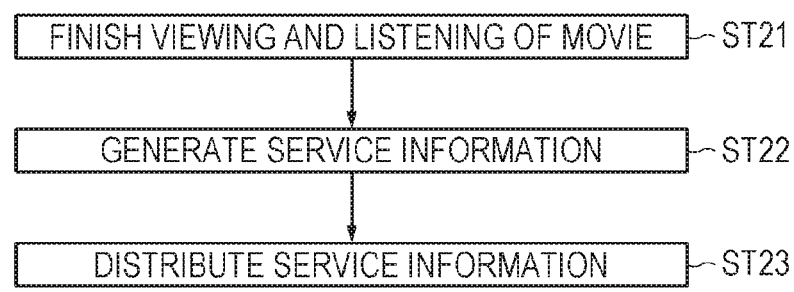
FIG. 15 is a diagram illustrating an example of emotion information.
FIG. 16 is a flowchart illustrating a flow of processing performed after viewing and listening of a movie.

As a result of the emotion estimation by the emotion estimation unit 33, emotion information is obtained. FIG. 15 illustrates a part of an example of the emotion information. The emotion information is, for example, data in which the movie (content type), the scene, the seat information, and the estimated value corresponding to a predetermined emotion are associated. In the specific example illustrated in FIG. 15, AA3 is described as information for specifying the movie, scene numbers 1, 2, and 3 are described, 0035 is described as the seat information, the estimated value (for example, 82.2) corresponding to the surprise emotion is described, and the estimated value (for example, 20.5) corresponding to the sadness emotion is described. The emotion estimation unit 33 supplies the emotion information to the communication unit 34. The communication unit 34 supplies the supplied emotion information to the server 2.

Note that the reaction information obtained in time series may be associated with a time stamp different from a scene. Furthermore, the reaction information obtained in time series may be associated with other metadata (for example, a chapter or production intention information of a filmmaker) instead of the time information of the movie.

[4. Generation of Service Information]

(4-1. Flow of Processing after Viewing and Listening of Movie)

FIG. 16 is a flowchart illustrating a flow of processing performed after the user U viewed and listened to the movie. In step ST21, viewing and listening of the movie ends. The emotion information is estimated on the basis of the sensor information at the time of viewing and listening of the movie of the user U, and the emotion information is transmitted to the server 2. Random data may be superimposed on the emotion information to secure security when the emotion information is transmitted (also referred to as differential privacy or the like). Then, the processing proceeds to step ST22.

In step ST22, the service information generation unit 23 of the server 2 generates the service information on the basis of the emotion information. Then, the processing proceeds to step ST23. In step ST23, the generated service information is distributed. For example, the generated service information is distributed to the reservation terminal 1. The distribution to the reservation terminal 1 is performed by, for example, sending a guide regarding the service information to the reservation terminal 1 by an e-mail and accessing an address on the network described in the guide by the user U. The service information may be displayed on the display unit 12 of the reservation terminal 1 by the user holding the reservation terminal 1 over a terminal installed in the movie theater after viewing and listening of the movie, or the service information may be distributed using a specific application. Furthermore, means for the distribution is not limited to an electronic medium, and the service information printed on a paper may be provided to the user U.

(4-2. Operation Example of Service Information Generation Unit)

Processing after viewing and listening of the movie will be specifically described. The emotion information is transmitted from the reaction information acquisition device 3 to the server 2, and the emotion information is received by the communication unit 24 of the server 2. The emotion information is supplied from the communication unit 24 to the service information generation unit 23.

Figure 17:
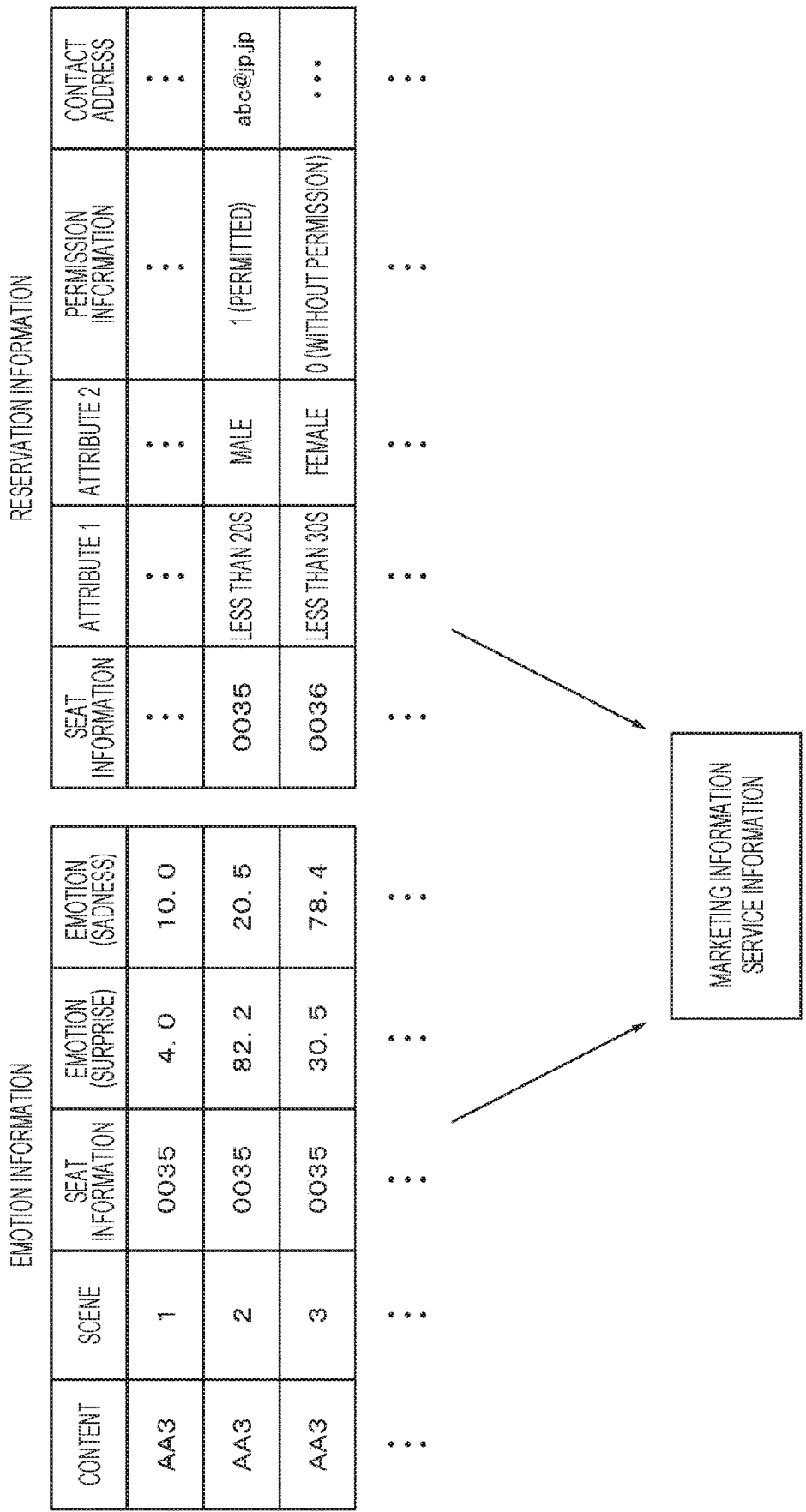
FIG. 17 is a diagram for describing processing of generating service information according to the embodiment.

FIG. 17 illustrates an example of the emotion information transmitted from the reaction information acquisition device 3 and an example of the reservation information managed by the reservation information management unit 22. Since the emotion information is similar to the emotion information illustrated in FIG. 15, duplicate description is omitted. The reservation information is, for example, information in which the seat information indicating the seat reserved by the user U, the attributes of the user U who has reserved the seat, the permission information, and the contact information are associated with one another. The permission information is, for example, flags of logical values of "1" and "0". In the present embodiment, "1" indicates that permission regarding the use of the reaction information is "present", and "0" indicates that permission regarding the user of the reaction information is "absent". The contact address is, for example, an e-mail address of the reservation terminal 1. However, an e-mail address of another device or the like may be used. Furthermore, account information of the user U used in the reservation processing may be associated with the seat information or the like.

For example, the seat information 0035 of the reserved seat is associated with "less than 20s" and "male" as the attributes of the user U, is associated with "1" as the permission information, and is associated with a predetermined e-mail address. For example, the seat information 0036 of the reserved seat is associated with "30s" and "female" as the attributes of the user U, is associated with "0" as the permission information, and is associated with a predetermined e-mail address.

The service information generation unit 23 refers to the reservation information and extracts the seat information corresponding to the presence of permission from the emotion information. Then, for example, the marketing information is generated using the emotion information corresponding to the same seat information and the attribute of the user U described in the reservation information. The marketing information is information indicating, for example, what kind of emotion is exhibited by the user U having what kind of attribute in which scene of what kind of movie. This kind of marketing information allows filmmakers to recognize what kind of movies and scenes are easily accepted by which regions and attributes, so the marketing information can be reflected in the production of the next movie. In particular, in the present embodiment, since a merit is obtained by estimating the emotion information for a publicly released movie and permitting the use of the emotion information, there is a high possibility that a lot of emotion information can be used and meaningful marketing information can be easily obtained. Note that the effect of obtaining the user's preference to the movie together with the emotion information can be obtained by providing the service of the present embodiment in a limited environment such as a preview, not in a publicly available movie. Here, the marketing information can include information corresponding to the service information to be described below.

(4-3. Specific Example of Service Information)

In the present embodiment, the service information is provided to the user as a merit of permitting the use of the emotion information. The service information generation unit 23 refers to the reservation information, extracts the seat information corresponding to the presence of permission from the emotion information, and generates the service information using the emotion information corresponding to the seat information. The service information is, for example, a characteristic of the user U based on the reaction information. Specific examples of the service information will be described with reference to FIGS. 18A, 18B, and 18C.

Figure 18A:
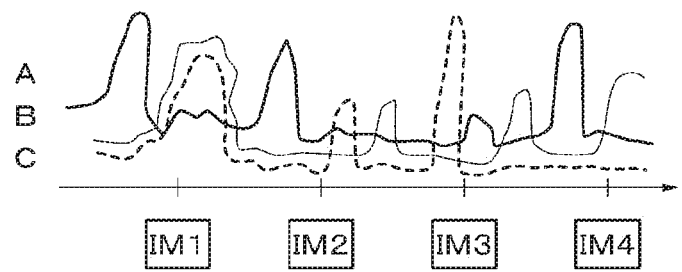
FIGS. 18A, 18B, and 18C are diagrams for describing a plurality of examples of the service information.

The service information illustrated in FIG. 18A is obtained by associating a graph illustrating changes in emotion A, emotion B, and emotion C, more specifically, changes in estimated values of the emotions with the time series of the movie. Note that the emotions A to C can be anything such as joy, surprise, and the like. Although the time series of the movie may be indicated by time information, in the present example, representative scenes (scenes 1 to 4) are displayed as thumbnail images (reduced images) IM1 to IM4 to make it easier for user U to understand. Note that the graph may be one referred to as a heat map display or the like that illustrates the emotion as a change in color intensity instead of the change in line. Furthermore, in the graph, a predetermined emotion being held may be presented in a case where a certain reference value is exceeded or may be presented for each scene, as illustrated in FIGS. 14B and 14C. By making such a presentation, the user U can look back at his/her emotional changes in connection with the time series and scenes of the movie.

Figure 18B:
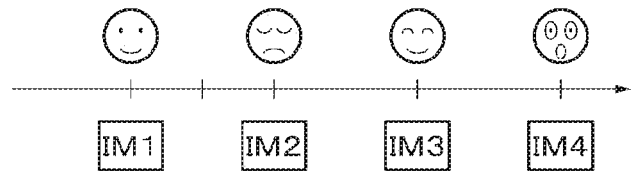

The service information illustrated in FIG. 18B is substantially similar to the service information illustrated in FIG. 18A, but an icon corresponding to an emotion (for example, an icon representing a facial expression) is used instead of a graph illustrating a change in an emotion.

Figure 18C:
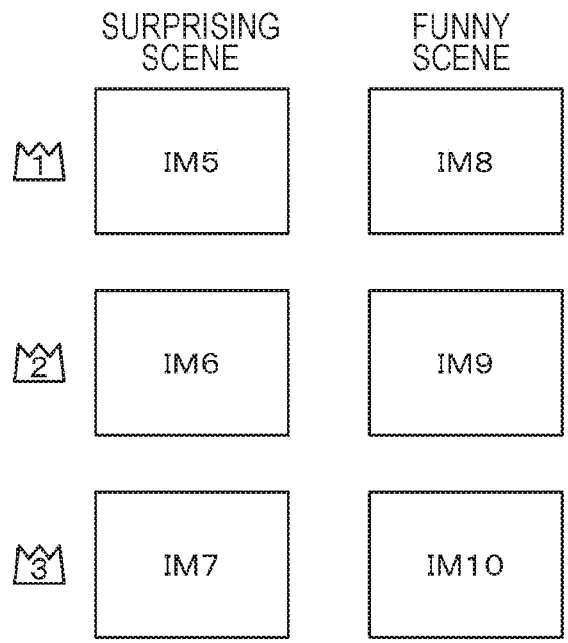

The service information may be information in which scenes causing uplifting feelings are displayed in a ranking format. For example, as illustrated in FIG. 18C, top three scenes with high estimated values corresponding to the surprise emotion and top three scenes with high estimated values corresponding to fun emotion are presented as the service information. The scenes are respectively represented by thumbnail images IM5 to IM10.

Figure 19:
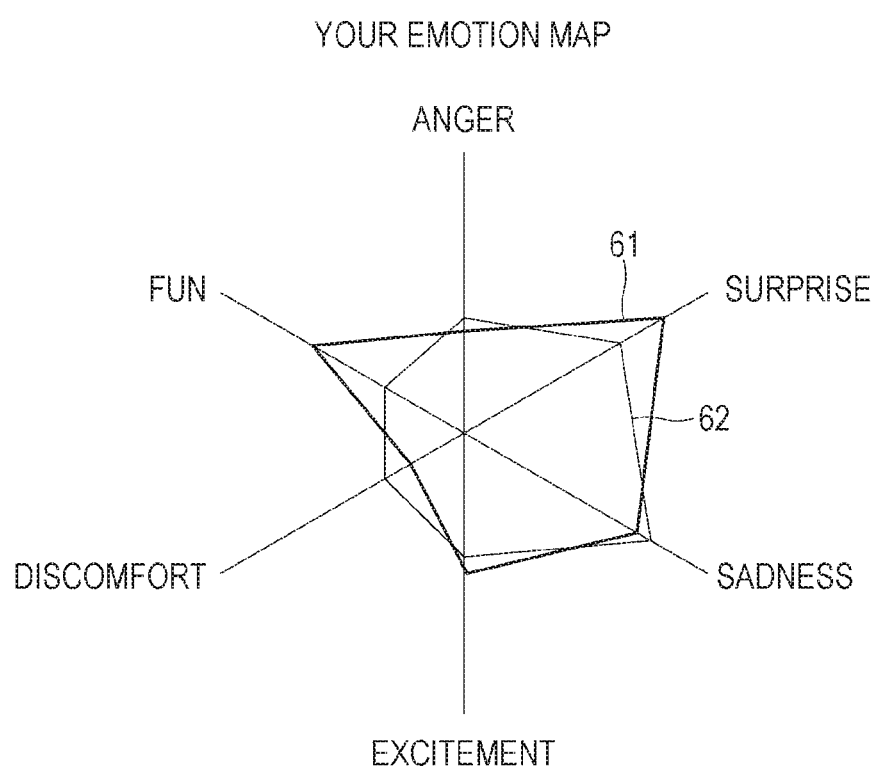
FIG. 19 is a diagram for describing another example of the service information.

The examples in FIGS. 18A, 18B, and 18C illustrate absolute characteristics based only on the emotion information regarding a certain user U. However, the presented information may be a relative characteristic such as the position of the user U's emotion information in the emotion information of other users U. For example, the emotion map as illustrated in FIG. 19 may be used. In the emotion map illustrated in FIG. 19, six emotions (anger, surprise, sadness, excitement, discomfort, and fun) are defined as an example, and the degree of each emotion felt by the user U at the time of viewing and listening of the movie is mapped on the emotion map as a graph 61. Furthermore, an average of the degrees of each emotion felt by another user U is mapped on the emotion map as a graph 62. By looking at this emotion map, a certain user U can recognize the difference in how to feel the movie from another user U. The data to be compared may be the emotion information of a user having the same attribute as the user U, may be the entire emotion information, or may be both. Furthermore, the service information is not limited to the emotion map, and may be a contrast between a scene that the user U has significantly reacted with and a scene that another user U has significantly reacted with. Note that the service information illustrated in FIGS. 18A, 18B, 18C, and 19 may be displayed together. Note that such comparison with other users may be performed in the presentation method in FIGS. 18A, 18B and 18C.

Additional information may be included in the service information illustrated in FIGS. 18A, 18B, 18C, and 19. Examples of such additional information include presentation of a recommended movie based on the emotion information. The recommended movie here can be selected from a category that is presumed to be preferred by a user who has such emotions by contrasting the movie with the emotion information. For example, for the user U who feels a lot of anger while viewing and listening of a movie, if a user who has similar emotions tends to like action movies, an action movie is presented to the user U as the recommended movie. Similarly, a romance movie can be presented to the user U who feels a lot of sadness as the recommended movie. The additional information may be presented as a result of personality assessment. For example, for the user U who feels a lot of sadness, a personality assessment result of "compassionate" may be presented as the additional information. Furthermore, for the user U who has little emotional change, a personality assessment result of "calm" may be presented as the additional information.

A feedback on the service information may be made. For example, as illustrated in FIG. 20A, a thumbnail image IM11 corresponding to a scene where the user U is most surprised is displayed on the basis of the emotion information on the display unit 12 as the service information. A display 71 for selecting whether or not the displayed scene is really the most surprising scene for the user U is displayed at a location close to the thumbnail image IM11. The user U selects whether or not the result indicated by the service information matches his/her subjective recognition using, for example, the reservation terminal 1. The selection result is transmitted from the reservation terminal 1 to the server 2 as feedback information. Note that the user U is not forced to perform the selection and the selection may not be made. The feedback information transmitted to the server 2 is associated with the corresponding emotion information. In a case where the feedback information is obtained, the emotion information may be corrected with the feedback information. Furthermore, the feedback information may be used for processing of improving a learning model for predicting the emotion information of the corresponding user U or a user U having the same attribute as the user U.

As described above, in a case where two seats are reserved with one account of a certain user U, for example, there is a high possibility that lovers or a couple will view and listen to the movie. In such a case, information related to the users U who uses the respective two seats may be presented as the service information. FIGS. 20A and 20B illustrate example of such service information. For example, the emotion information is estimated for each of the two seats, and scenes where emotional tendencies of the users U at the seats are the same or close are displayed as thumbnail images IM12 to IM14 as sympathetic scenes. Furthermore, scenes where the users U have separately reacted (have certain emotions strongly) are displayed as thumbnail images IM15 and IM16, respectively. Moreover, a display 72 regarding compatibility is displayed. For example, a probability (%) that the compatibility becomes higher as the number of sympathetic scenes is larger is displayed.

Note that the two users U may not be lovers or couples, but may be friends or a parent and a child. Therefore, the group relationship (couple, lovers, friends, parent and child, or the like) may be displayed together so that the user can select the actually relevant relationship. The compatibility assessment may be performed by a different algorithm according to a selection result. In addition, a movie that the users U can sympathize with or a movie that is considered preferable for understanding each other may be extracted on the basis of the emotion information, and the result may be presented as the service information.

In a case where a preliminary quiz about the movie is performed at the time of the reservation processing, an answer to the quiz may be presented as the service information.

As described above, the user U can receive presentation of the service information by permitting the use of the emotion information. By receiving the provision of the service information, the user U can look back on changes in his/her emotions at the time of viewing and listening of the movie. In addition, the user U can obtain various types of information according to the service information, such as characteristics of the emotion he/she has about the movie and the compatibility with the partner. As described above, by providing the user with the acquired emotion information as representative service information, the user can be motivated to permit the use of the emotion information, and more users can be prompted to permit the user of the emotion information. Of course, in a case where the user does not want the service information, the user can simply reject the use of the emotion information in the reservation processing.

[5. Processing in a Case where there is No Permission to Use Reaction Information]

Here, processing performed in a case where there is no permission to use the reaction information will be described. In the case where there is no permission to use the reaction information, corresponding data is discarded. For example, the service information generation unit 23 of the server 2 refers to the reservation information, reads the seat information corresponding to the permission information of "0", and discards (deletes) the data of the emotion information corresponding to the seat information. Furthermore, the server 2 may use only the data of the emotion information corresponding to the seat information associated with the permission information of "1". Furthermore, the server 2 may use only permitted information.

The reservation information may be supplied from the server 2 to the reaction information acquisition device 3. Then, the emotion estimation unit 33 may refer to the reservation information, perform the emotion estimation only for the sensor information supplied from the sensor unit 32 provided corresponding to the seat information with the permission information of "1", and output the result of the emotion estimation. Furthermore, the reservation information may be supplied to the sensor unit 32. Then, the sensor unit 32 may output the sensor information to the emotion estimation unit 33 only in a case where the permission information corresponding to the seat where the sensor unit 32 itself is provided is "1". By determining the content of the permission information in the reaction information acquisition device 3, the processing load on the sensor unit 32 and the emotion estimation unit 33 can be reduced.

Note that the reaction information may be mixed in and stored with other data without being associated with the user's attributes. In other words, the reaction information may be stored in a form where the information cannot be identified as personal information (made meaningless) (keeping personal information unconnected). Alternatively, the obtained data can be used in a form of being not linked to personal information by statistically processing the obtained data. As described above, it is not always necessary to discard the reaction information regarding the user who has not given permission. At this time, a difference may be provided in handling the reaction information between the user who has permitted the use and the user who has not permitted the use, such as the information being used in conjunction with the attribute information for the user who has permitted the use, whereas the information being used without being linked to the personal information for the user who has not permitted the use.

2. Modification

The embodiment of the present disclosure has been specifically described. However, content of the present disclosure is not limited to the above-described embodiment, and various modifications based on the technical idea of the present disclosure can be made.

In the above-described embodiment, a movie has been described as an example of the presented information. However, the presented information is not limited to a movie. For example, the presented information may be a drama, a storytellers' theater, a live performance, sports watching, an advertisement before the playback of a main part of a movie, an art exhibition, or the like. In particular, the present technology can be provided for an art exhibition or the like, and an artist can know what feelings a viewer has in which work. In this case, for example, the permission information is input at the time of purchasing an appreciation ticket.

Figure 21:
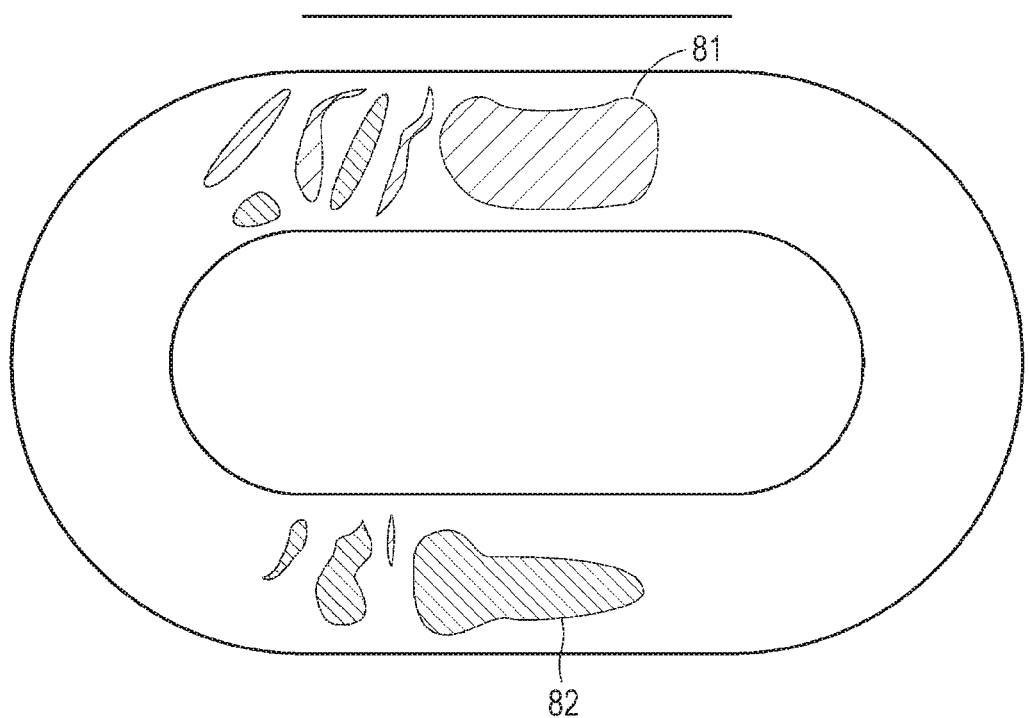
FIG. 21 is a diagram for describing modifications.

Furthermore, the present disclosure can be applied not only to a content presentation-type event such as a movie but also to a participation-type event. Examples of the participation-type event include horse racing and bicycle race watching, and theme park attractions. For example, a distribution of the reaction information in a stadium as illustrated in FIG. 21 is created on the basis of the reaction information of audience. For example, the audience in a place with hatching 81 is uplifted, and the audience in a place with hatching 82 is calm. In this way, the reaction information is visualized for each support team, support target (horse for horse racing), and audience attribute. As a result, for example, it is possible to visualize a state in which the audience in 10s is excited but the audience in 30s is calm. Using the reaction information, a temporal change in excitement of the audience so far or a heat map of the reaction information in audience seats may be created. The visualized reaction information is displayed on a screen in a stadium or distributed in real time to a mobile terminal owned by a user who has permitted the use of the reaction information. Thereby, the user U can recognize an excitement situation in a stadium or a theme park.

The functions in the information processing system 100 in the above-described embodiment can be performed by an arbitrary device. For example, the server 2 may include the emotion estimation unit 33 and the server 2 may estimate the emotion information. In this case, only the sensor information is transmitted from the reaction information acquisition device 3 to the server 2. To reduce a bandwidth in communication, only characteristic data (for example, characteristic points in face recognition) of the sensor information may be transmitted.

Alternatively, the reaction information acquisition device 3 may include the service information generation unit 23. Then, the reaction information acquisition device 3 may generate the service information and transmit the generated service information to the reservation terminal 1. Moreover, the reaction information acquisition device 3 may have all the functions of the server 2, or the information processing system 100 may be configured by the reservation terminal 1 and the reaction information acquisition device 3. By appropriately changing the configuration in this way, the reaction information acquisition device 3 may function as an information processing device.

Some playback devices that play back a Blu-ray disc (BD) (registered trademark), a digital versatile disc (DVD), and the like have a function called digest playback that plays back a shortened version of a main story. A disc creator may produce the disc by determining a digest playback location and a delimiter (chapter) in the main story using the reaction information permitted to be used. For example, the disc may be produced such that digest playback is performed around a portion where many users are surprised, excited, or moved. The user who has permitted the use of the reaction information may be able to produce a disc reflecting his/her reaction information. The reaction information may be reflected not only on a disc but also on reproduction of content distributed via the network.

The camera module 32A in the above-described embodiment may be an imaging device such as a smartphone, a mobile phone, or a tablet computer carried by the user U, instead of being provided in a movie theater. By mounting such an imaging device on a support tool provided on, for example, a front seat, images of the user U may be captured. An image captured by the imaging device is supplied to the emotion estimation unit 33 by communication. Note that such mounting of the imaging device on the support tool may be determined that the use of the reaction information has been permitted.

The emotion estimation unit 33 may target a specific emotion such as surprise or impression and determine the presence or absence of the target emotion. The target emotion may be changed for each scene of the movie, or the target emotion may be changed according to the content of the presented information.

The service information may be presented by voice instead of or together with the display.

The present disclosure can be implemented as a system including a plurality of devices, or a device constituting the system, as well as by a method, a program, or the like.

The present disclosure can also employ the following configurations.

(1)

An information processing device including:
 a reaction information use unit configured to use reaction information indicating a reaction of a user to presented information in a case where use of the reaction information has been permitted.

(2)

The information processing device according to (1), further including:
 a reaction information acquisition unit configured to acquire the reaction information.

(3)

The information processing device according to (2), in which the reaction information acquisition unit includes a sensor unit and a reaction information estimation unit that estimates the reaction information on the basis of sensor information output from the sensor unit.

(4)

The information processing device according to (3), in which the sensor unit monitors a user existing in a predetermined range, and outputs the sensor information regarding the user to the reaction information estimation unit in a case where the user has permitted the use of the reaction information.

(5)

The information processing device according to (3) or (4), in which the reaction information estimation unit estimates the reaction information for each user, using sensor information of all of users existing in a predetermined range, and outputs only the reaction information of the user who has permitted the use of the reaction information.

(6)

The information processing device according to any one of (1) to (5), in which the reaction information use unit generates service information to be presented only to the user who has permitted the use of the reaction information.

(7)

The information processing device according to (6), in which the service information is a characteristic based on the reaction information of the user.

(8)

The information processing device according to (6), in which the service information is at least one of a characteristic based on the reaction information of the user or a characteristic relative to reaction information of another user.

(9)

The information processing device according to any one of (1) to (8), in which permission information indicating presence or absence of the permission is associated with information regarding a seat reserved by the user.

(10)

The information processing device according to (9), in which, in a case where a plurality of pieces of the seat information corresponding to a predetermined user exists, and the permission information indicates the presence of the permission, the reaction information use unit generates information related to a plurality of users located at the seat information, using the reaction information of the users.

(11)
The information processing device according to any one of (1) to (10), in which the reaction information is information corresponding to an emotion of the user.

(12)
The information processing device according to any one of (1) to (11), in which the presented information is any one of content viewed and listened to by the user, a sport watched by the user, and an art appreciated by the user.

(13)
An information processing method including:
by a reaction information use unit, using reaction information indicating a reaction of a user to presented information in a case where use of the reaction information has been permitted.

(14)
An information processing system including:
a reaction information acquisition unit configured to acquire reaction information indicating a reaction of a user to presented information; and
a reaction information use unit configured to use the reaction information in a case where use of the reaction information has been permitted.

(15)
The information processing system according to (14), in which the reaction information acquisition unit includes a sensor unit and a reaction information estimation unit that estimates reaction information on the basis of sensor information output from the sensor unit.

(16)
A display device including:
a display control unit configured to perform control of displaying, on a display unit, seat information at a time of appreciating predetermined presented information, an input screen as to whether or not to permit use of reaction information indicating a reaction of a user at the time of appreciating the presented information, and information for prompting the permission, in a series of reservation processing for reserving a seat indicated by the seat information.

(17)
A reservation system including:
the display device according to (16); and an information processing device connected to the display device, in which
the information processing device includes a reservation information management unit that manages permission information indicating presence or absence of the permission output from the display device and the reserved seat information in association with each other.

REFERENCE SIGNS LIST

1 Reservation terminal
2 Server
3 Reaction information acquisition device
11 Reservation terminal control unit
12 Communication unit
22 Reservation information management unit
23 Service information generation unit
32 Sensor unit
33 Emotion estimation unit

The invention claimed is:
1. An information processing device, comprising:
at least one sensor configured to monitor a first user within a specific range of the at least one sensor; and
a central processing unit (CPU) configured to:
change a setting value of the at least one sensor based on a change in a brightness of presented information on a display screen,
wherein
the change in the brightness of the presented information is in synchronization with a progress of the presented information, and
the at least one sensor is further configured to generate sensor information based on the changed setting value;
estimate, based on the sensor information, reaction information that indicates a reaction of the first user to the presented information; and
use the reaction information in a case where the use of the reaction information has been permitted by the first user.

2. The information processing device according to claim 1, wherein the CPU is further configured to acquire the reaction information.

3. The information processing device according to claim 1, wherein the CPU is further configured to:
estimate the reaction information for each user, using the sensor information of a plurality of users existing in the specific range, wherein the plurality of users comprises the first user; and
output only the reaction information of the first user who has permitted the use of the reaction information.

4. The information processing device according to claim 1, wherein the CPU is further configured to generate service information to be presented only to the first user who has permitted the use of the reaction information.

5. The information processing device according to claim 4, wherein the service information is a characteristic based on the reaction information of the first user.

6. The information processing device according to claim 4, wherein the service information is at least one of a characteristic based on the reaction information of the first user or a characteristic associated with reaction information of a second user.

7. The information processing device according to claim 4, wherein
the reaction information is information corresponding to an emotion of the first user and an emotion of a second user, and
the service information indicates a change in the emotion of the first user and the emotion of the second user with respect to a time-series of the presented information.

8. The information processing device according to claim 1, wherein
the CPU is further configured to use the reaction information based on permission information, and
the permission information indicates a presence or an absence of a permission of the first user with respect to seat information regarding a seat reserved by the first user.

9. The information processing device according to claim 8, wherein,
in a case where a plurality of pieces of the seat information corresponding to the first user exists, and the permission information indicates the presence of the permission, the CPU is further configured to generate information related to a plurality of users associated with the seat information, using the reaction information of each user of the plurality of users, and
the plurality of users comprises the first user.

10. The information processing device according to claim 1, wherein the reaction information is information corresponding to an emotion of the first user.

11. The information processing device according to claim 1, wherein the presented information is one of content viewed and listened to by the first user, a sport watched by the first user, or an art appreciated by the first user.

12. The information processing device according to claim 1, wherein the CPU is further configured to change a dynamic range of the at least one sensor in synchronization with the progress of the presented information.

13. An information processing method, comprising:
monitoring, by at least one sensor, a user within a specific range of the at least one sensor;
changing, by a central processing unit (CPU), a setting value of the at least one sensor based on a change in a brightness of presented information on a display screen,
wherein the change in the brightness of the presented information is in synchronization with a progress of the presented information;
generating, by the at least one sensor, sensor information based on the changed setting value;
determining, by the CPU, reaction information based on the sensor information,
wherein the reaction information indicates a reaction of the user to the presented information; and
using, by the CPU, the reaction information in a case where the use of the reaction information has been permitted by the user.

14. An information processing system, comprising:
at least one sensor configured to monitor a user within a specific range of the at least one sensor; and
a central processing unit (CPU) configured to:
acquire reaction information that indicates a reaction of the user to presented information;
change a setting value of the at least one sensor based on a change in a brightness of the presented information on a display screen,
wherein
the change in the brightness of the presented information is in synchronization with a progress of the presented information, and
the at least one sensor is further configured to generate sensor information based on the changed setting value;
estimate the reaction information based on the sensor information; and
use the reaction information in a case where the use of the reaction information has been permitted by the user.

15. A device, comprising:
a first central processing unit (CPU) configured to control a display unit to display:
seat information at a time of appreciation of presented information,
an input screen to obtain a user input for one of a permission or a rejection for a use of reaction information at the time of appreciation of the presented information, wherein
the reaction information indicates a reaction of a user to the presented information, and
the reaction information is based on sensor information generated by at least one sensor,
information to prompt the permission, in a series of reservation processing for reserving a seat indicated by the seat information, and
service information only to the user who has permitted the use of the reaction information, wherein the service information indicates a change in the reaction of the user with respect to a time-series of the presented information; and
a second CPU configured to:
change a setting value of the at least one sensor based on a change in a brightness of the presented information on a display screen, wherein
the change in the brightness of the presented information is in synchronization with a progress of the presented information, and
the at least one sensor generates the sensor information based on the changed setting value; and
estimate the reaction information based on the sensor information.

16. A reservation system, comprising:
a display device comprising:
a first central processing unit (CPU) configured to control a display unit to display:
seat information at a time of appreciation of presented information;
an input screen to obtain a user input for one of a permission or a rejection for a use of reaction information at the time of appreciation of the presented information, wherein
the reaction information indicates a reaction of a user to the presented information, and
the reaction information is based on sensor information generated by at least one sensor;
information to prompt the permission, in a series of reservation processing to reserve a seat indicated by the seat information; and
service information only to the user who has permitted the use of the reaction information, wherein the service information indicates a change in the reaction of the user with respect to a time-series of the presented information; and
an information processing device connected to the display device,
wherein the information processing device includes a second CPU configured to:
manage permission information indicating a presence or an absence of the permission outputted from the display device;
manage the seat information in association with the permission information;
change a setting value of the at least one sensor based on a change in a brightness of the presented information on a display screen, wherein
the change in the brightness of the presented information is in synchronization with a progress of the presented information, and
the at least one sensor generates the sensor information based on the changed setting value; and
estimate the reaction information based on the sensor information.

* * * * *